(12) United States Patent
Armstrong

(10) Patent No.: US 8,486,867 B2
(45) Date of Patent: *Jul. 16, 2013

(54) METHOD OF FRACTURING USING MANNANOHYDROLASE ENZYME BREAKER

(75) Inventor: Charles David Armstrong, Tomball, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/294,082

(22) Filed: Nov. 10, 2011

(65) Prior Publication Data

US 2012/0055670 A1     Mar. 8, 2012

Related U.S. Application Data

(63) Continuation-in-part of application No. 12/579,771, filed on Oct. 15, 2009, now Pat. No. 8,058,212.

(51) Int. Cl.
    *C09K 8/60*     (2006.01)

(52) U.S. Cl.
    USPC .......................................... 507/201; 435/262

(58) Field of Classification Search
    None
    See application file for complete search history.

(56) References Cited

U.S. PATENT DOCUMENTS

| | | | |
|---|---|---|---|
| 5,067,566 A | 11/1991 | Dawson |
| 5,165,477 A | 11/1992 | Shell et al. |
| 5,201,370 A | 4/1993 | Tjon-Joe-Pin |
| 5,224,544 A | 7/1993 | Tjon-Joe-Pin et al. |
| 5,226,479 A | 7/1993 | Gupta et al. |
| 5,247,995 A | 9/1993 | Tjon-Joe-Pin et al. |
| 5,421,409 A | 6/1995 | Mueller et al. |
| 5,437,331 A | 8/1995 | Gupta et al. |
| 5,441,109 A | 8/1995 | Gupta et al. |
| 5,547,026 A | 8/1996 | Brannon et al. |
| 5,562,160 A | 10/1996 | Brannon et al. |
| 5,566,759 A | 10/1996 | Tjon-Joe-Pin et al. |
| 5,806,597 A | 9/1998 | Tjon-Joe-Pin et al. |
| 5,874,558 A | 2/1999 | Boel et al. |
| 5,881,813 A | 3/1999 | Brannon et al. |
| 6,110,875 A | 8/2000 | Tjon-Joe-Pin et al. |
| 6,138,760 A | 10/2000 | Lopez et al. |
| 6,186,235 B1 | 2/2001 | Tjon-Joe-Pin et al. |
| 6,197,506 B1 | 3/2001 | Fodor et al. |
| 6,197,566 B1 | 3/2001 | Knap et al. |
| 6,566,114 B1 | 5/2003 | Kauppinen et al. |
| 6,936,454 B2 | 8/2005 | Kelly et al. |
| 7,255,169 B2 * | 8/2007 | van Batenburg et al. .. 166/280.2 |
| 7,294,498 B2 | 11/2007 | Bylina et al. |
| 2006/0258542 A1 | 11/2006 | Segura |

FOREIGN PATENT DOCUMENTS

EP      0912725 B1      7/2004

OTHER PUBLICATIONS

Lüthi, E., et. al.; Cloning, Sequence Analysis, and Expression in *Escherichia coli* of a Gene Coding for a β-Mannanase from the Extremely Thermophilic Bacterium "Caldocellum saccharolyticum;" Applied and Environmental Microbiology; Mar. 1991; pp. 694-700; American Society for Microbilogy.

Daniel D. Morris et al., "Correction of the β-Mannanase Domain of the celC Pseudogene from Caldocellulosiruptor saccharolyticus and Activity of the Gene Product on Kraft Pulp", Applied and Environmental Microbiology, Jun. 1995, vol. 61, No. 6, pp. 2262-2269.

Database UniProt [Online] Mar. 24, 2009, "SubName: Full=Mannan endo-1,4-beta-mannosidase., Cellulase; EC=3.2.1.4; EC=3.2.1.78; Flags: Precursor;", retrieved from EBI accession No. UNIPROT:B9MKU6.

Database UniProt [Online] Mat 1, 2000, "SubName: Full=Multidomain beta-1,4-beta-mannanase; Flags: Precursor;", retrieved from EBI accession No. UNIPROT:Q9RFX5.

* cited by examiner

*Primary Examiner* — Nashaat Nashed
(74) *Attorney, Agent, or Firm* — John Wilson Jones; Jones & Smith, LLP

(57) ABSTRACT

A thermophilic mannanohydrolase enzyme may be used as an enzyme breaker for fracturing fluids containing hydratable polymers of guar and underivatized guar. The amino acid sequence of the mannanohydrolase is at least 90% homologous to the amino acid sequence of SEQ ID NO:2.

20 Claims, 9 Drawing Sheets

5'
GGATCCATGCGCCTGAAAACCAAAATCCGCAAAAAGTGGCTGTCAGTGCTGT
GCACTGTAGTCTTTCTGCTGAATATTCTGTTTATTGCGAACGTTACCATCCTGC
CAAAAGTAGGCGCGGCTACCTCCAACGATGGTGTGGTTAAAATTGATACCTC
GACCCTGATTGGTACCAATCATGCTCATTGCTGGTATCGCGATCGTCTGGATA
CCGCGCTGCGCGGAATTCGTAGTTGGGGTATGAACTCGGTACGCGTCGTTCTG
TCTAATGGCTATCGCTGGACAAAAATTCCGGCCAGCGAAGTTGCCAACATTA
TTTCGCTGTCCCGCTCCCTGGGCTTCAAAGCCATTATTCTGGAGGTGCATGAT
ACCACCGGTTACGGTGAAGATGGTGCGGCGTGCTCCCTGGCACAGGCAGTTG
AATATTGGAAAGAGATCAAAGCGTGCTGGATGGCAATGAAGATTTTGTCAT
CATCAATATTGGTAATGAACCGTATGGTAATAACAACTATCAGAACTGGGTA
AATGATACTAAGAATGCAATTAAAGCGCTGCGCGATGCCGGCTTTAAGCATA
CCATCATGGTAGATGCGCCGAACTGGGGCCAGGATTGGTCGAATACCATGCG
CGACAATGCTCAGTCTATTATGGAAGCCGATCCACTGCGTAATCTGGTATTTA
GCATTCACATGTACGGTGTCTATAATACTGCGAGCAAAGTGGAAGAATATAT
CAAAAGTTTTGTGGATAAAGGTCTGCCGCTGGTTATCGGCGAATTCGGTCACC
AGCACACTGATGGTGACCCTGATGAAGAGGCGATCGTTCGCTATGCCAAACA
GTATAAAATTGGCCTGTTTAGTTGGAGTTGGTGTGGGAACAGCAGTTACGTC
GGTTACCTGGATATGGTGAATAACTGGGACCCGAACAACCCGACCCCATGGG
GGCAGTGGTATAAAACAAATGCGATCGGCACGTCAAGCACGCCGACCCCGA
CATCGACTGTCACCCCAACGCCACCGCCGCGCCAGCACCAGCATCGCCAATA
AAAGCTT
3'

*FIG. 1A*

MRLKTKIRKKWLSVLCTVVFLLNILFIANVTILPKVGAATSNDGVVKIDTSTLIGT
NHAHCWYRDRLDTALRGIRSWGMNSVRVVLSNGYRWTKIPASEVANIISLSRSL
GFKAIILEVHDTTGYGEDGAACSLAQAVEYWKEIKSVLDGNEDFVIINIGNEPYG
NNNYQNWVNDTKNAIKALRDAGFKHTIMVDAPNWGQDWSNTMRDNAQSIME
ADPLRNLVFSIHMYGVYNTASKVEEYIKSFVDKGLPLVIGEFGHQHTDGDPDEEA
IVRYAKQYKIGLFSWSWCGNSSYVGYLDMVNNWDPNNPTPWGQWYKTNAIGT
SSTPTPTSTVTPTPPPRQHQHRQ*

*FIG. 1B*

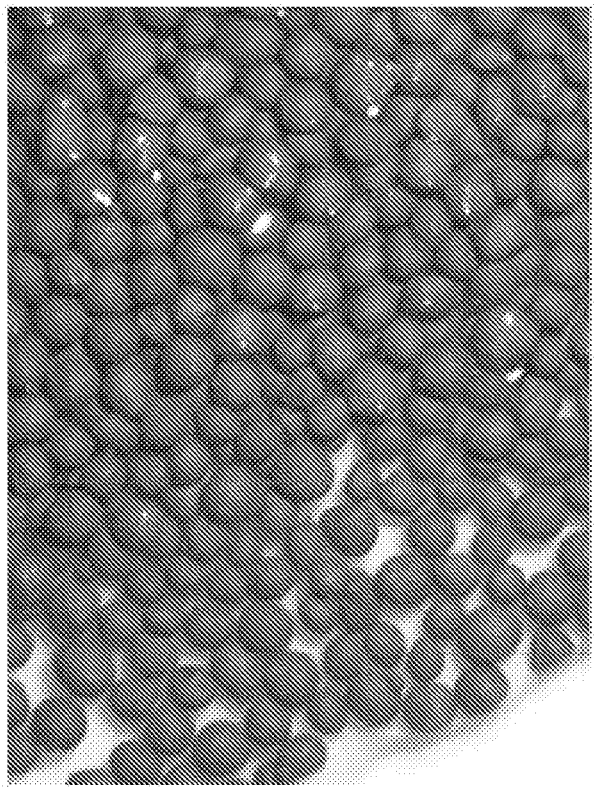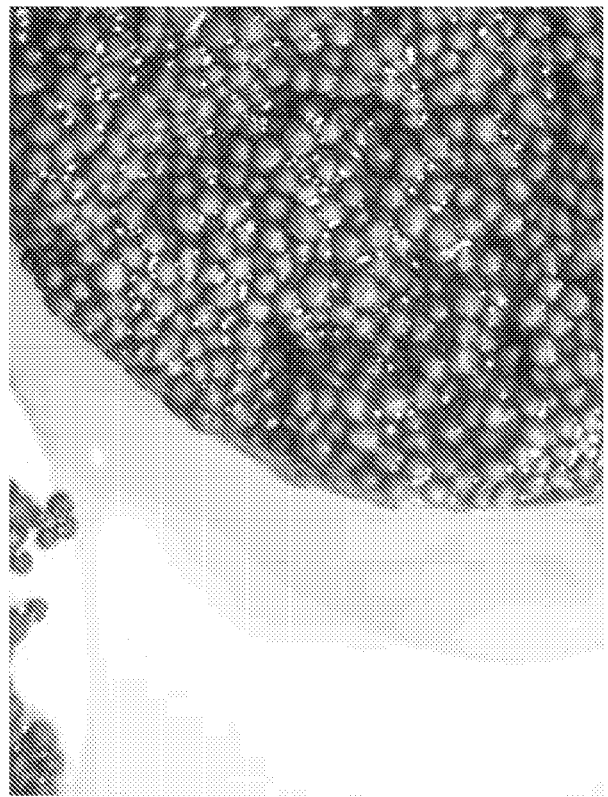
FIG. 8

METHOD OF FRACTURING USING MANNANOHYDROLASE ENZYME BREAKER

This application is a continuation-in-part application of U.S. patent application Ser. No. 12/579,771, filed Oct. 15, 2009, now U.S. Pat. No. 8,058,212, herein incorporated by reference.

FIELD OF THE INVENTION

An isolated mannanohydrolase enzyme which hydrolyzes galactomannan substrates at temperatures in excess of 160° F. has particular applicability as an enzyme breaker in fracturing fluids containing guar and derivatized guars.

BACKGROUND OF THE INVENTION

Hydraulic fracturing is used to create subterranean fractures that extend from the borehole into rock formation in order to increase the rate at which fluids can be produced by the formation. Generally, a high viscosity fracturing fluid is pumped into the well at sufficient pressure to fracture the subterranean formation. In order to maintain the increased exposure to the formation, a solid proppant is added to the fracturing fluid which is carried into the fracture by the high pressure applied to the fluid.

Greater than 65% of conventional fracturing fluids are made of guar gum (galactomannans) or guar gum derivatives such as hydroxypropyl guar (HPG), carboxymethyl guar (CMG) and carboxymethylhydroxypropyl guar (CMHPG). These polymers can be crosslinked in order to increase their viscosities and increase their capabilities of proppant transport.

Once the high viscosity fracturing fluid has carried the proppant into the formation, breakers are used to reduce the fluid's viscosity which allows the proppant to settle into the fracture and thereby increase the exposure of the formation to the well. Breakers work by reducing the molecular weight of the polymers, thus 'breaking' the polymer. The fracture then becomes a high permeability conduit for fluids and gas to be produced back to the well.

Chemical oxidizers and enzymes are most commonly used as breakers. The oxidizer produces a radical which then degrades the polymer. This reaction is limited by the fact that oxidizers are stoichiometric and they will attack not only the polymer but any molecule that is prone to oxidation. Enzymes, on the other hand, are catalytic and substrate specific and will catalyze the hydrolysis of specific bonds on the polymer. An enzyme will degrade many polymer bonds in the course of its lifetime. Unfortunately, enzymes operate under a narrow temperature range and their functional states are often inactivated at high temperatures.

Conventional enzymes used to degrade galactomannans work well at ambient to moderate temperatures (75° F. to 150° F.). At elevated temperatures, (>150° F.) these enzymes quickly denature and lose activity. The beta-mannanase enzyme used in conventional enzyme formulations has a temperature maximum of approximately 150° F. Activity profiles have indicated that the enzyme retains little to no activity past this point. Because many downhole fracturing operations are conducted at temperatures in excess of 150° F., it would be beneficial to have an enzyme that can degrade guar-based fracturing fluids under these elevated temperatures.

SUMMARY OF THE INVENTION

A mannanohydrolase enzyme effectively hydrolyzes galactomannins and has particular effectiveness in the hydrolysis of guar polymers at elevated temperature ranges. The high temperature mannanohydrolase enzyme may be associated with glutathione S-transferase (GST) or may be unassociated from GST.

The nucleotide sequence encoding the mannanohydrolase enzyme was derived from the β-mannanase gene of *Caldocellum saccharolyticum* and codon optimized for expression in *E. coli*. The gene coding for the mannanohydrolase (hereinafter "htβ") has the nucleotide sequence set forth in FIG. 1A (SEQ ID NO:1) which is codon optimized to increase the expression of the mannanohydrolase in *E. coli*. The gene htβ (SEQ ID NO:1) may then be cloned into suitable plasmid vectors, such as pUC57, pUC 19, and pGS-21a, or into any other commercially available or custom expression or cloning vector. The mannanohydrolase can be transformed and expressed in commercially available *Escherichia coli* strains. The translated amino acid sequence of the mannanohydrolase is shown in FIG. 1B (SEQ ID NO:2).

An aqueous fracturing fluid may then be prepared which contains the enzyme, guar polymer and crosslinking agent.

When used in hydraulic fracturing, the mannanohydrolase is effective in degrading guar based polymers at temperatures in excess of 160° F.

BRIEF DESCRIPTION OF THE DRAWINGS

In order to more fully understand the drawings referred to in the detailed description of the present invention, a brief description of each drawing is presented, in which:

FIG. 1A (SEQ ID NO:1) represents the nucleotide sequence that codes for the mannanohydrolase used in the invention. FIG. 1B (SEQ ID NO:2) represents the amino acid sequence of the mannanohydrolase enzyme.

FIG. 8A shows a photomicrograph of a proppant pack made in the absence of the mannanohydrolase enzyme.

FIG. 8B shows a proppant pack made in the presence of the mannanohydrolase enzyme.

DETAILED DESCRIPTION OF THE PREFERRED EMBODIMENTS

The high temperature enzyme used in the fracturing method of the invention is referred to herein as "mannanohydrolase" when it is unassociated with glutathione S-transferase (GST) and "GST-mannanohydrolase" when it is the fusion of β-mannanase and GST.

The mannanohydrolase enzyme described herein originates from the thermophilic and anaerobic *Caldocellum saccharolyticum*. Isolation of the gene encoding for the β-mannanase enzyme is described in E. Luthi et al, "Cloning, Sequence Analysis, and Expression in *Escherichia coli* of a Gene Coding for a β-Mannanase From the Extremely Thermophilic Bacterium '*Caldocellum saccharolyticum*'", *Applied and Environmental Microbiology*, March 1991, pp. 694-700, herein incorporated by reference.

The gene for the mannanohydrolase enzyme was then codon optimized to increase the efficiency of its expression in *E. coli*. The nucleotide sequence of the htβ gene is set forth in FIG. 1A (SEQ ID NO:1). This nucleotide sequence has a 74% homology to the sequence depicted in FIG. 2 of Luthi et al for the mannanase gene. The nucleotide sequence includes the coding sequence for the mannanohydrolase and the leader sequence on the N-terminus.

Figure 2:
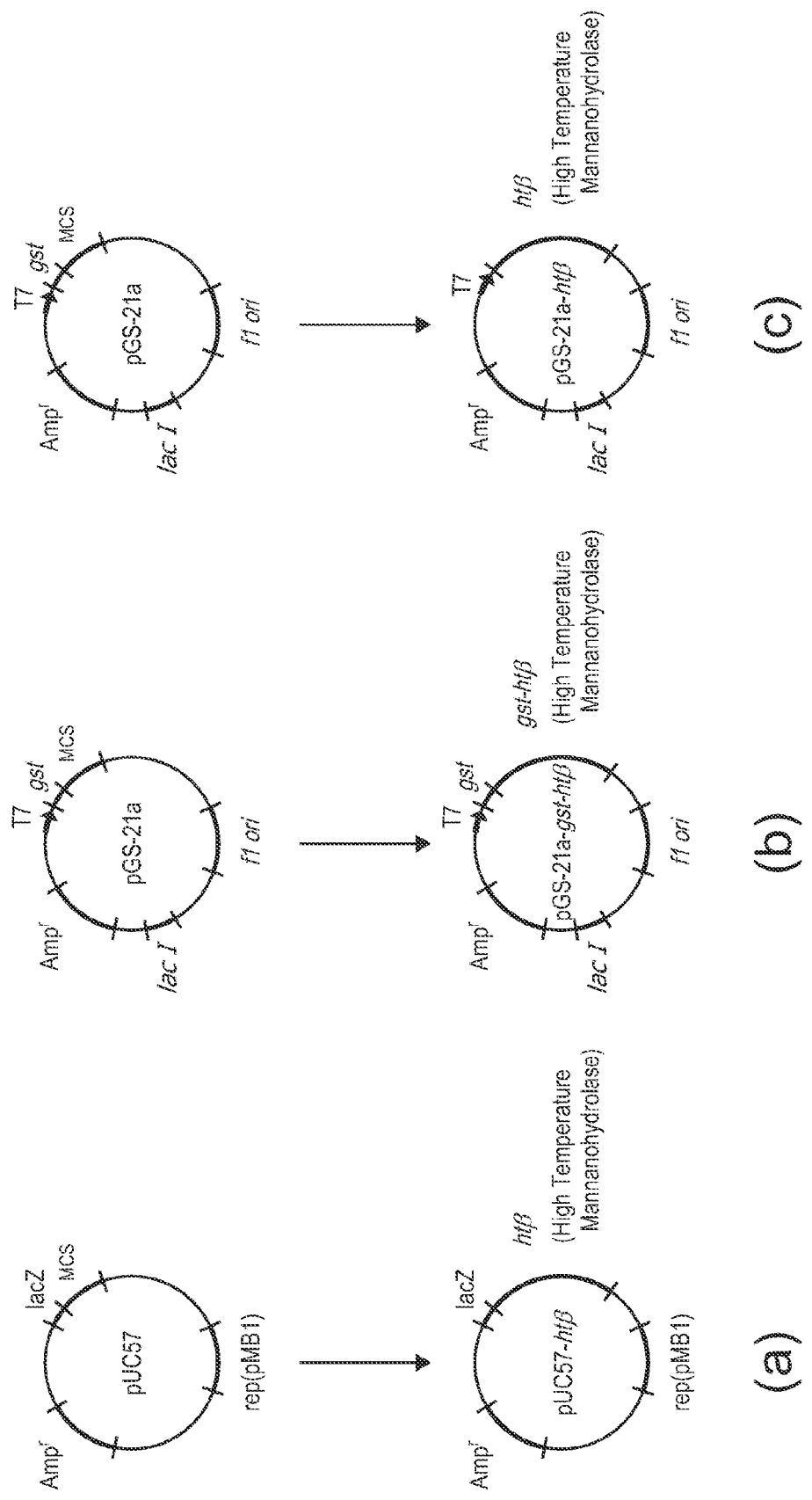
FIG. 2 represents creation of the plasmids pUC57-htβ, pGS-21a-gst-htβ and pGS-21-htβ harboring the mannanohydrolase gene.

As illustrated in FIG. 2 (*a*), the htβ gene may be cloned into cloning vector pUC57 to create the plasmid pUC57-htβ. In (b) and (c), the gene may be cloned into expression vector pGS-21a which contains a coding region for GST protein. In (b), the resultant gene codes for a GST-mannanohydrolase fusion product. In (c), the resultant gene codes for an enzyme without the GST fusion tag. Expression using the pGS-21a-gst-htβ and pGS-21a-htβ plasmid of (b) and (c) respectively produces mannanohydrolase fused to the N-terminal GST protein and mannanohydrolase without the associated GST protein, respectively.

In each of FIGS. 2 (*a*), (*b*) and (*c*), Amp$^r$ regulates the expression of β-lactamase, rep(pMB1) and f1 ori represents the origin in pUC57 and pGS-21a, respectively, responsible for the replication of the plasmid, lacI codes for the lactose repressor, T7 represents the T7 RNA polymerase promoter and MCS represents the Multiple Cloning Site. The 5' end of the optimized sequence contains a BamHI restriction endonuclease site and the 3' end contains a HindIII restriction endonuclease site for cloning into the pGS-21a expression vector to create the GST-mannanohydrolase fusion protein. Alternatively, the 5' BamH1 site was replaced with an NdeI restriction endonuclease site to create the mannanohydrolase protein without the associated GST fusion.

The plasmids pGS-21a-htβ, pGS-21a-gst-htβ and pUC57-htβ may be transformed into commercially available *E. coli* strains and cultured. The cells may then be harvested, lysed, and the resultant solution used as a cell lysate. A cell free extract can be produced by removing the cell debris from the lysate, and the enzyme can then be isolated from the extract. The term "isolated" denotes that the enzyme has been removed from intact cells or cellular debris and, in a condition other than its native environment, is free of other extraneous or unwanted nucleic acids, proteases, and lipids, in a form suitable for use as a breaker for fracturing fluids.

The gene coding for the mannanohydrolase enzyme may further have a nucleotide sequence which is substantially homologous to the nucleotide sequence of FIG. 1A (SEQ ID NO:1). The term "substantially homologous" is used herein to denote nucleotides having at least 75%, more preferably at least 80%, more preferably at least 85%, and even more preferably at least 90%, sequence identity to the sequence shown in FIG. 1A (SEQ ID NO:1).

The translated amino acid sequence of the mannanohydrolase is shown in FIG. 1B (SEQ ID NO:2). Typically, the translated amino acid sequence of the mannanohydrolase enzyme used in the hydraulic fracturing method described herein is at least 60% similar to the translated amino acid sequence set forth in FIG. 1B (SEQ ID NO:2).

In a preferred form, the isolated protein is substantially free of other proteins. It is preferred to provide the protein in a greater than 40% pure form, more preferably greater than 60% pure form. Even more preferably it is preferred to provide the protein in a highly purified form, i.e., greater than 80% pure, more preferably greater than 95% pure, and even more preferably greater than 99% pure, as determined by SDS-PAGE.

The mannanohydrolase effectively hydrolyzes the guar polymer at elevated temperature ranges, such as in excess of 72° F. typically over pH ranges between from about 5.0 to about 11.0. The mannanohydrolase may hydrolyze the guar polymer at temperatures in excess of 160° F. as well as in excess of 180° F. In fact, the mannanohydrolase may hydrolyze the guar polymer at temperatures in excess of 185° F. and even in excess of 195° F. In addition, the mannanohydrolase may be used in combination with other enzymes and/or oxidative breakers to degrade guar gels over broader temperature and pH ranges.

The aqueous fracturing fluid used in the invention may be prepared by blending a hydratable polymer into an aqueous fluid. The aqueous fluid could be, e.g., water, brine, or water-alcohol mixtures. Any suitable mixing apparatus may be used for this procedure. In the case of batch mixing, the hydratable polymer and aqueous fluid are blended for a period of time which is sufficient to form a hydrated sol. The hydratable polymer is added to the aqueous fluid in concentrations ranging from about 0.10% to 5.0% by weight of the aqueous fluid. The most preferred range for the present invention is about 0.20% to 0.80% by weight. The pH of the fracturing fluid may generally range from about 5.0 to about 11.0, typically about 6.0 or higher, more typically about 6.5 or higher. In one embodiment, the pH of the fracturing fluid may be about 7.0 or higher or about 7.5 or higher. In another embodiment, the pH of the fracturing fluid may be about 8.0 or about 8.5 or higher. In a preferred embodiment, the pH of the fracturing fluid is greater than or equal to 9.0 and more preferably greater than or equal to about 9.5.

The hydratable polymer useful in the present invention is underivatized guar as well as derivatized guars. Underivatized guar is preferred. Examples of derivatized guars include hydroxypropyl guar, carboxymethyl hydroxypropyl guar, and carboxymethyl hydroxyethyl cellulose.

In addition to the enzyme breaker and hydratable polymer, the fracturing fluid includes a crosslinking agent. The crosslinking agent can be polymers with metal ions including aluminum, antimony, zirconium and titanium containing compounds including the so-called organotitanates as well as borates and boron releasing compounds. In the case of the borate crosslinkers, the crosslinking agent is any material which supplies borate ions. Suitable borate crosslinkers include organoborates, monoborates, polyborates, mineral borates, boric acid, sodium borate, including anhydrous or any hydrate, borate ores such as colemanite or ulexite as well as any other borate complexed to organic compounds to delay the release of the borate ion. Borate crosslinking agents are preferred.

The crosslinking agent is preferably present in the range from about 0.001% to in excess of 0.5% by weight of the aqueous fluid. Preferably, the concentration of crosslinking agent is in the range from about 0.005% to about 0.25% by weight of the aqueous fluid.

Typically, the enzyme is introduced as an aqueous enzyme solution. The weight percentage of enzyme solution in the treatment fluid is dependent upon the number of units of enzyme activity in the aqueous enzyme solution. For instance, the amount of an aqueous enzyme solution having 30,000 units of enzyme activity in the treatment fluid is generally between from about 0.05 to about 1.3 weight percent, preferably from about 0.103 to about 0.206 weight percent. The weight percentage of an enzyme solution containing a different unit of enzyme activity may be determined using the designated weight percentage for the enzyme solution containing 30,000 units of enzyme activity.

The optimum pH of the aqueous fluid containing the crosslinkable polymer is alkaline and typically is between from about 9.5 to about 11.0.

The fracturing fluids of the invention also may have a pH regulating substance incorporated therein as a companion material to the enzyme breaker. The pH regulating substance is any substance which is initially inert but slowly hydrolyzes in the gelled fracturing fluid to produce a Bronsted acid, thereby gradually lowering the pH of the gelled fluid and activating the enzyme breaker. The preferred pH regulating substances include organic anhydrides, acyl halides, sulfonyl halides, benzylic halides and low molecular weight esters which slowly hydrolyze to produce Bronsted acids. By "low molecular weight" ester is meant that the ester should be soluble in the fracturing fluid in order to accomplish its intended purpose of hydrolyzing with time to produce an acid. Generally, the higher the molecular weight, the less soluble the ester. As a result, lower molecular weight esters are preferred for ease of use. Preferably, the pH regulating substance is a low molecular weight ester selected from the group consisting of ethyl acetate, 2-ethoxyethylacetate, ethylacetoacetate, triethylcitrate, methylbenzoate and dimethylphthalate. Typical molecular weights for the 2-ethoxyethylacetate, ethylacetoacetate and triethylcitrate used in the examples which follow are 132, 130 and 276 respectively. Preferably, the pH regulating substance is present in the range from about 0.01% to about 0.85% by weight of the aqueous fluid.

The well treatment fluid may be prepared on location using a high shear foam generator or may be shipped to the desired location.

The fracturing fluid may further contain a proppant which are normally added to the fluid prior to the addition of the crosslinking agent. Once transported into the formation by the fracturing fluid, a pack of proppant may be formed within the created or enlarged fracture to hold the fracture open during production of fluid from the formation. It is desirable that the proppant pack be capable of forming a partial monolayer of proppant in the fracture to provide increased interconnected interstitial spaces between abutting proppant particulates. Increased fracture conductivity results since the produced fluids typically flow around the widely-spaced proppant particulates rather than through the interstitial spaces in a packed bed.

In an aspect, the amount of proppant in the fracturing fluid may be between about 0.5 to about 12.0, pounds of proppant per gallon of fracturing fluid. Preferably, it may be between from about 0.25 to about 4.0 pounds per gallon of fracturing fluid.

Suitable proppants include those conventionally known in the art including quartz sand grains, glass beads, aluminum pellets, ceramics, plastic beads, including polyamides, and ultra lightweight (ULW) particulates such as ground or crushed shells of nuts like walnut, coconut, pecan, almond, ivory nut, brazil nut, etc.; ground and crushed seed shells (including fruit pits) of seeds of fruits such as plum, olive, peach, cherry, apricot, etc.; ground and crushed seed shells of other plants such as maize (e.g., corn cobs or corn kernels), etc.; processed wood materials such as those derived from woods such as oak, hickory, walnut, poplar, mahogany, etc., including such woods that have been processed by grinding, chipping, or other form of particalization, processing, etc.

Further the proppant may include porous ceramics or organic polymeric particulates. The porous particulate material may be treated with a non-porous penetrating material, coating layer or glazing layer. For instance, the porous particulate material may be a treated particulate material, as defined in U.S. Patent Publication No. 20050028979 wherein (a) the ASG of the treated porous material is less than the ASG of the porous particulate material; (b) the permeability of the treated material is less than the permeability of the porous particulate material; or (c) the porosity of the treated material is less than the porosity of the porous particulate material.

The propping agents are normally used in concentrations between about 1 to 8 pounds per gallon of fracturing fluid composition, but higher or lower concentrations can be used as required.

The fracturing fluid can also contain other conventional additives common to the well service industry such as surfactants, corrosion inhibitors, crosslinking delaying agents and the like.

In a typical fracturing operation, the fracturing fluid of the invention is pumped at sufficiently high pressures to cause the formation or enlargement of fractures and to place proppant into the fracture.

The following examples are illustrative of some of the embodiments of the present invention. All percentages set forth in the Examples are given in terms of weight units except as may otherwise be indicated.

EXAMPLES

Example 1

The htβ gene was cloned into cloning vector pUC57 to create the plasmid pUC57-htβ and into expression vector pGS-21a to create the pGS-21a-htβ plasmid. The plasmids pGS-21a-htβ and pUC57-htβ were then transformed into competent BL21(DE3) or DH5α $E.$ $coli$ strains and cultured in 5 mL LB-Miller nutrient media at 98.6° F. at 200 rpm for 16 hours. The culture broth was supplemented with 100 ug/mL ampicillan which was used as an inoculum for a 100 mL culture of $E.$ $coli$ harboring the plasmids pGS-21a-htβ or pUC57-htβ. These cultures were grown at 98.6° F. and 200 rpm. After 4 hours, isopropyl β-D-1-thiogalactopyranoside (IPTG) was added to the culture to a final concentration of 0.1 mM. After 3 hours of incubation in the presence of IPTG, the cells were chilled to 39° F. and harvested by centrifugation at 3,000 rpm for 20 minutes. The culture medium was then discarded and the cells stored at −4° F. until use. The cells were then thawed and resuspended in 5 mLs chilled 50 mM sodium phosphate buffer. Lysozyme was added to a final concentration of 1 mg/mL and the culture was incubated at room temperature for 30 minutes. Nucleic acids were disrupted by brief pulses of sonication and resultant cell free extract (CFX) was obtained by centrifugation.

Example 2

Figure 3:
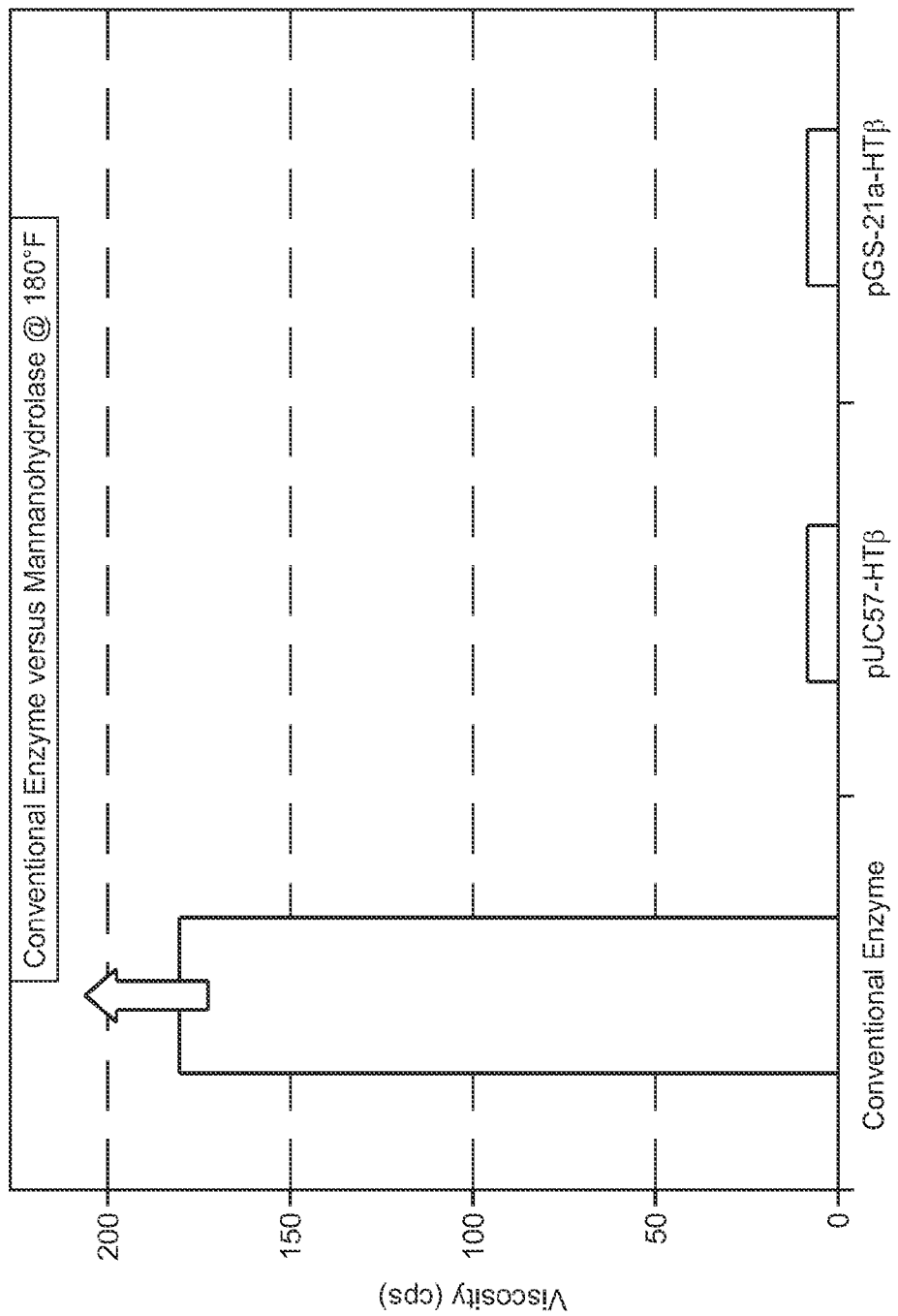
FIG. 3 contrasts reduction in viscosity after 18 hours at 180° F. of a 25 ppt borate crosslinked guar suspension containing the mannanohydrolase enzyme versus a suspension not containing the mannanohydrolase enzyme.

About 1 gpt of conventional beta-mannanase enzyme, commercially available as GBW-12CD from Baker Hughes Incorporated diluted in a 1:33 volumetric ratio in water, and about 2 mLs of the CFX of Example 1 containing pGS-21a-htβ and pUC57-htβ were added to 100 mL aqueous fluid containing 25 ppt GW3, 2gpt BF-7L and 1 gpt XLW-32 and incubated for 18 hours at 180° F. (GW-3 is a guar suspension agent, XLW-32 is a borate crosslinking agent, and BF-7L is a buffering agent, all of which are commercially available from Baker Hughes Incorporated). The samples were then allowed to cool to room temperature and their viscosities measured using a Fann 35 viscometer. The results are shown in FIG. 3 wherein it is illustrated that the mannanohydrolase provides almost complete reduction in the viscosity of guar after 18 hours at 180° F. while the conventional enzyme product does not appear to be as effective in reducing the viscosity of the cross linked fluid at this temperature and pH. The arrow in FIG. 3 represents an unbroken sample. The initial pH of all samples was 10.5.

Example 3

Figure 4:
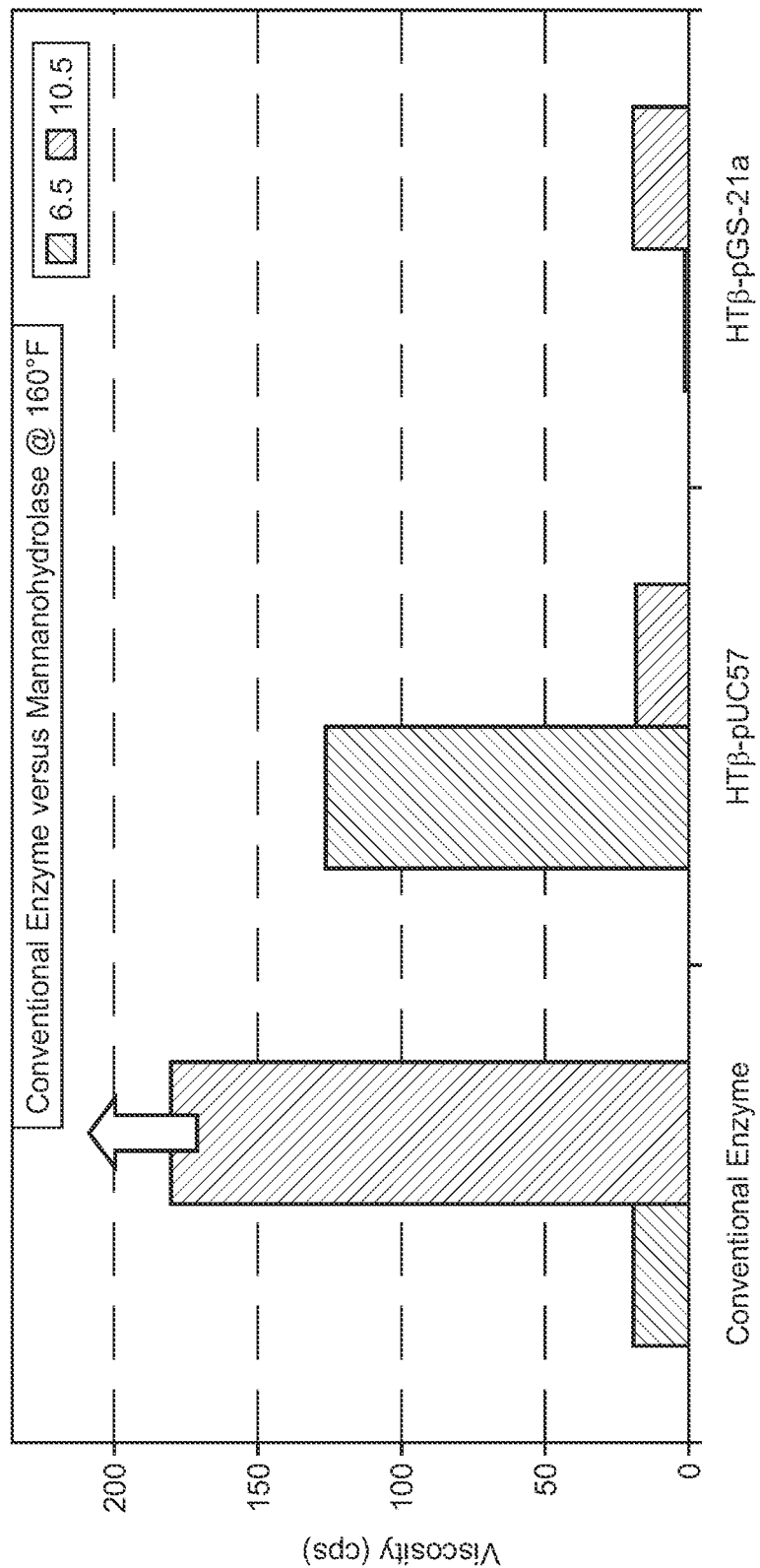
FIG. 4 contrasts reduction in viscosity after 18 hours at 160° F. of a 25 ppt borate crosslinked guar suspension containing the mannanohydrolase enzyme versus a suspension not containing the mannanohydrolase enzyme.

About 1 gpt of the conventional enzyme of Example 3 and of 2 mLs CFX from samples containing pGS-21a-htβ and pUC57-htβ from Example 1 were added to 100 mL aqueous samples containing 25 ppt GW-3, 2 gpt BF-7L and 1 gpt XLW-32 and incubated for 18 hours at 160° F. Samples of GW-3 were used at pH 6.5 and 10.5. The conventional enzyme, GBW-12, was shown to degrade the GW-3 sample at pH 6.5 but not at 10.5. Samples containing the mannanohydrolase provided partial to complete degradation of the crosslinked GW-3 after 18 hours at 160° F. Viscosities were measured on a Fann 35 and are shown in FIG. 4 wherein FIG. 4 represents the viscosity reduction in borate cross-linked 25 ppt GW-3 by the mannanohydrolase. The arrow represents an unbroken sample.

Example 4

Figure 5:
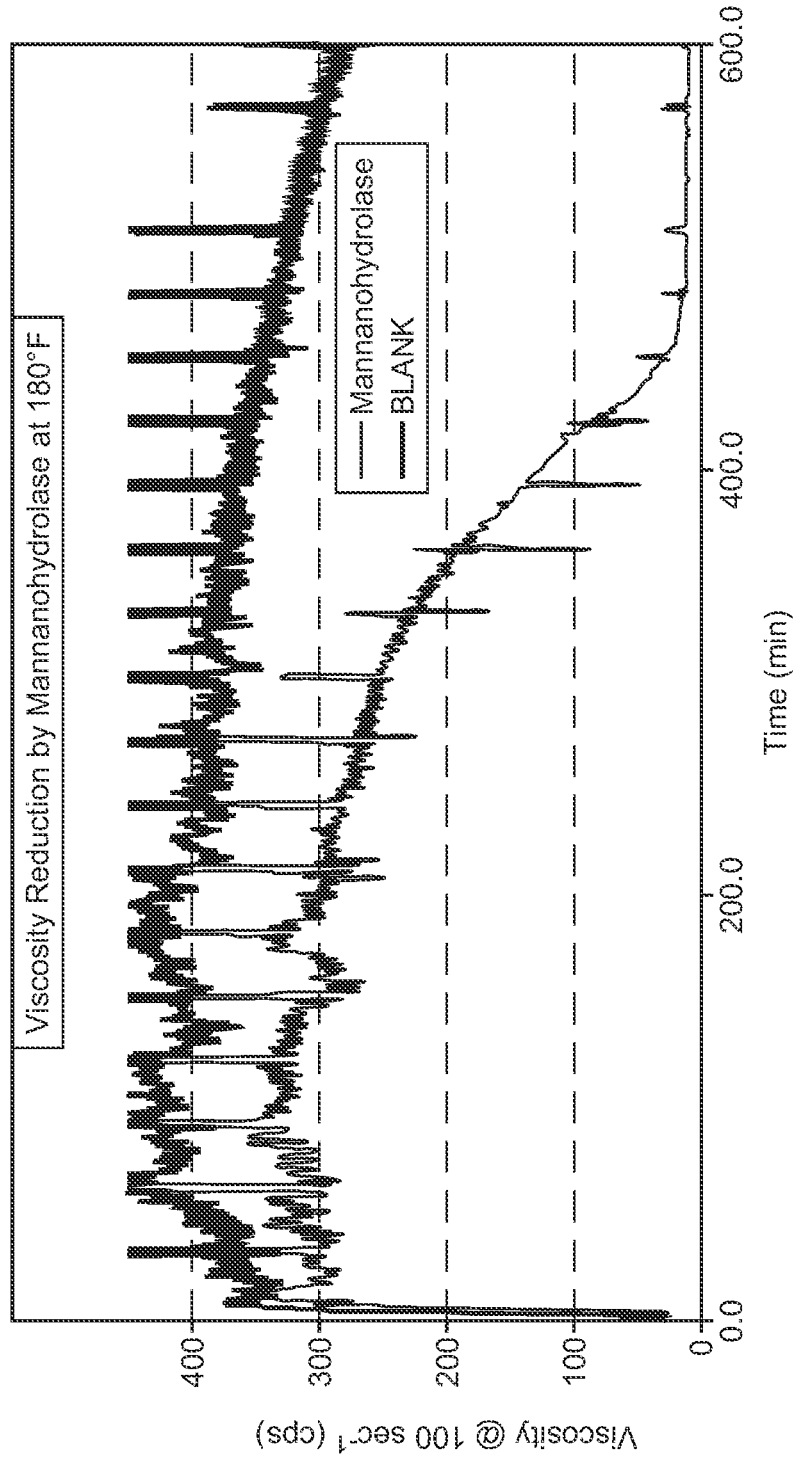
FIG. 5 contrasts reduction in viscosity over 10 hours at 180° F. of a borate crosslinked guar suspension containing the mannanohydrolase enzyme versus a suspension not containing the mannanohydrolase enzyme.
Figure 6:
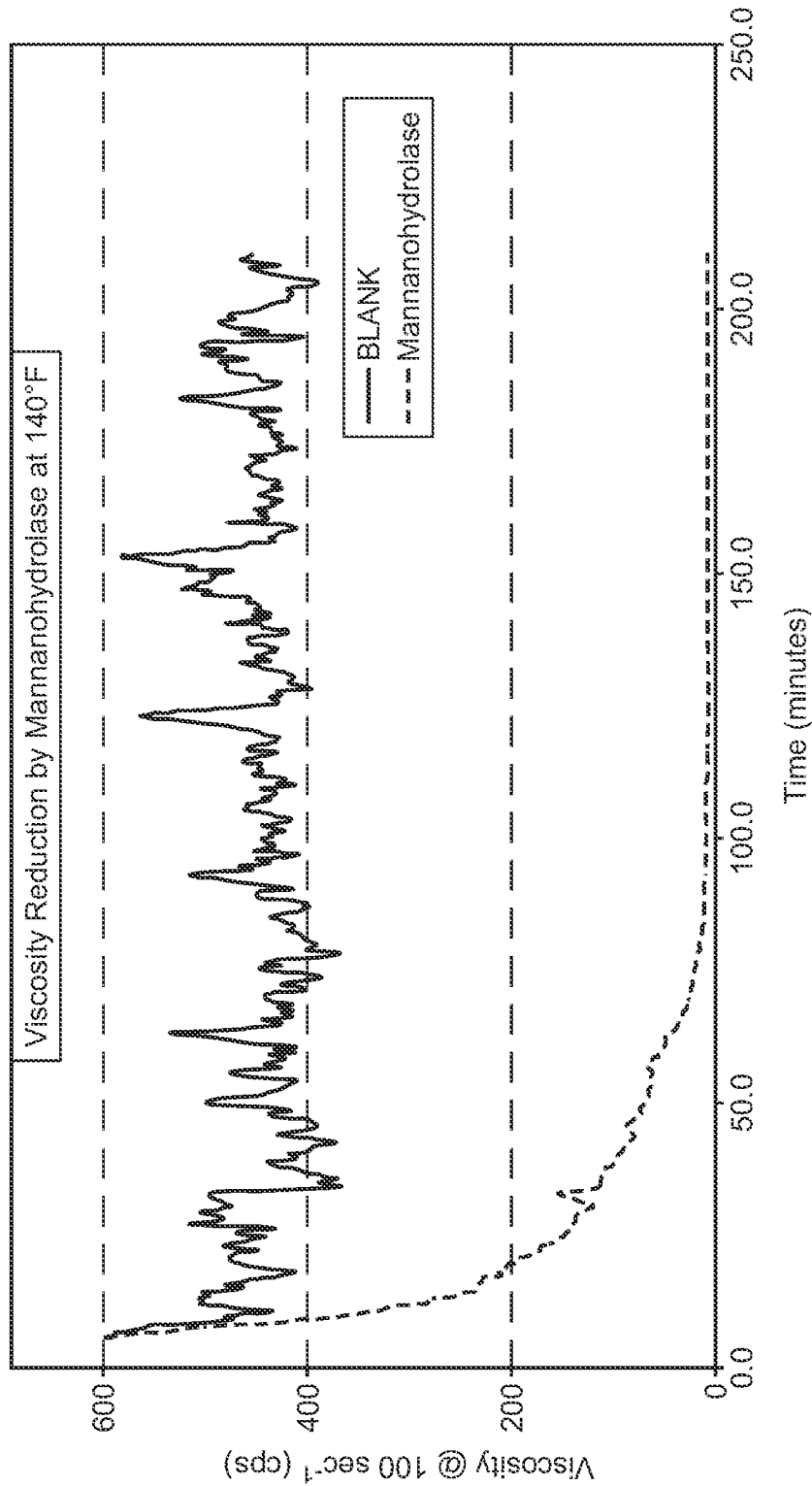
FIG. 6 contrasts reduction in viscosity over 3.5 hours at 140° F. of a borate crosslinked guar suspension containing the mannanohydrolase enzyme versus a suspension not containing the mannanohydrolase enzyme.

A 100 mL aqueous fluid was prepared containing 25 ppt GW3, 1.5 gpt BF-7L and 1.5 gpt of a borate ore crosslinker slurried in hydrocarbon oil, commercially available from Baker Hughes Incorporated as XLW-30. The pH1 of the solution was 10.8. Two samples were then prepared. One sample, designated (−), had no enzyme added to the fluid. The other sample, designated (+), had 0.75 gpt of a 1/25 dilution of mannanohydrolase CFX solution produced from the pGS21a-htβ expression vector. FIG. 5 represents the reduction in viscosity of the two samples over 10 hours at 180° F. FIG. 6 represents the reduction in viscosity of the two samples over 10 hours at 140° F.

Example 5

Figure 7:
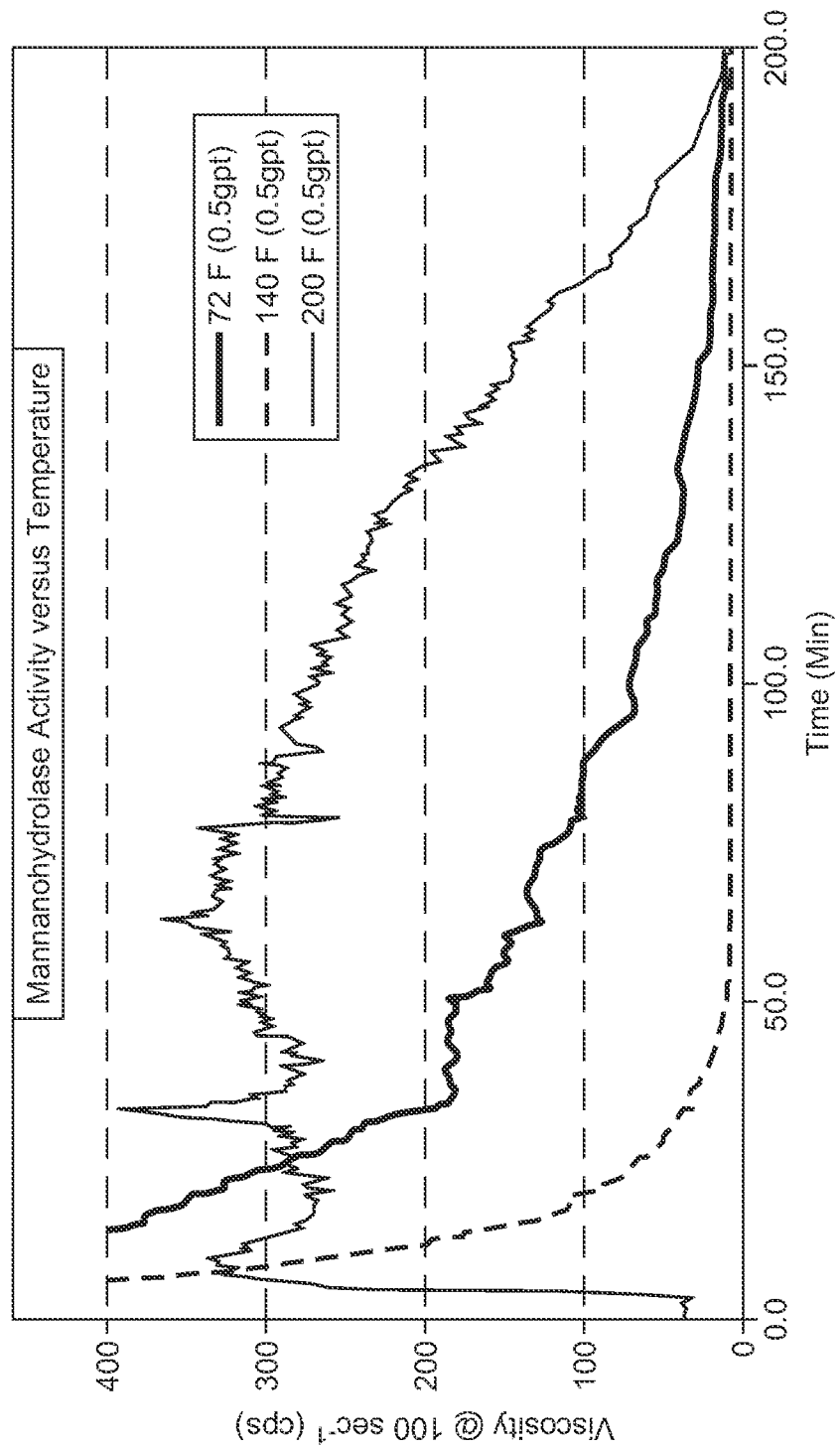
FIG. 7 contrasts reduction in viscosity over varying temperatures of a guar suspension containing the mannanohydrolase enzyme.

A 100 mL aqueous fluid was prepared containing 25 ppt GW3, 1.3 gpt BF-7L and 1.0 gpt XLW-32 crosslinker for tests at 72° F. and 140° F. A second 100 mL aqueous fluid was prepared containing 25 ppt GW3, 2.0 gpt BF-7L and 1.5 gpt XLW-30 crosslinker for tests at 200° F. In all samples, the mannanohydrolase enzyme concentration was 0.5 gpt. The rheology of each sample was measured on a Chandler HTHP 5550 viscometer at 100 sec$^{-1}$. FIG. 7 represents the rheology profiles of the tests at variable temperatures and demonstrates that mannanohydrolase is effective in reducing the viscosity of the crosslinked galactomannan polymer at a range of temperatures from 72° F. to at least 200° F.

Examples 2, 3, 4 and 5 demonstrate that fluids containing the mannanohydrolase effectively hydrolyze the guar polymer at elevated temperature and pH ranges where the conventional enzyme is not as effective.

Example 6

This example illustrates the regained conductivity of a proppant pack treated with an aqueous fluid which contains the mannanohydrolase enzyme breaker. Two samples of a 100 mL aqueous fluid were prepared containing 25 ppt GW-3, 1.5 gpt BF-7L and 1.3 gpt XLW-30. One sample further contained 1.25 gpt (1/5 dilution) of mannanohydrolase (referenced in Example 6); the other sample did not contain any Enzyme. A 60 mL syringe was equipped with a 30 mesh wire screen cut to the internal diameter of the syringe. The screen supported a piece of filter paper (2.5 μm pore size) which was also cut to the internal diameter of the syringe. 10 grams of 20/40 CarboProp, a proppant of Carbo Ceramics, was then applied to the filter paper. The 100 mL cross linked fluid was then applied to the proppant bed and forced through the proppant pack until the plunger came to rest on the top of the proppant pack. The end of the syringe was capped and the syringe submerged in a 180° F. water bath for 24 hours. The syringe was then removed from the water bath and allowed to cool to room temperature. The syringe was then inverted and the plunger gently removed to minimize disturbance to the proppant pack. The proppant pack was placed in a blue weigh boat and immediately visualized under a compound light microscope with 10× magnification. FIGS. 8A and 8B are photomicrographs of the proppant packs illustrating conductivity between a suspension which does not contain the mannanohydrolase (photomicrograph A) versus the suspension which does contain the mannanohydrolase (photomicrograph B).

As shown in photomicrograph A, the proppant pack had a highly defined structure signifying that the fracturing fluid remained crosslinked. (Remaining fluid from the syringe was also crosslinked.) Photomicrograph B illustrates proppant packs with no structure wherein the pack "fell apart" immediately upon removal from the syringe. The remaining fluid from the syringe was water-like with very low viscosity. Proppant packs from fluids containing the mannanohydrolase showed little to no crosslinked gel remaining. This suggests excellent cleanup and high recovery of proppant pack permeability.

Example 7

This example illustrates the production of then mannanohydrolase enzyme in a 10 liter fermentation process. The htβ gene was cloned into the expression vector pGS21-a with the restriction endonucleases NdeI and HindIII to create a mannanohydrolase without the associated GST fusion. The resultant expression vector was transformed into BL21(DE3) *E. coli* and plated on LB-Agar plates containing 100 ug/mL ampicillan. The plates were incubated at 98.6° F. overnight. A single colony was picked from the plate and used to inoculate 100 mLs of LB-Miller broth containing 100 ug/mL ampicillan. The culture was incubated at 98.6° F. overnight at 200 RPM.

The 100 mL overnight culture was used as an inoculum into 10 L of Terrific Broth in a Bioflow 3000 Fermentor from New Brunswick Scientific. Ampicillin was added to a final concentration of 100 ug/mL. The fermentation culture was grown for 24 hours at 98.6° F. with maximum agitation and feed with compressed air to maintain the maximum aeration possible. Glycerol was added at a rate of 4 mLs/hour for the full 24 hours. An antifoam solution was added as needed. Once the $OD_{600}$ reached a value of 0.5, a sterile solution of lactose was added to the mixture so that the final concentration of lactose in the system was 15 mM. After 24 hours, the cell culture was stored at 39° F. until further processing.

The cell culture was then homogenized and the cell debris removed either through centrifugation or filtration through a 0.2 um pore-size polyethersulfone membrane. The resultant solution could then be used as the mannanohydrolase enzyme solution or further concentrated as desired. In this example, the filtrate was concentrated via tangential flow filtration (TFF) using a 30,000 MWCO polyethersulfone filter. The retentate was then used as the mannanohydrolase enzyme solution.

Other embodiments within the scope of the claims herein will be apparent to one skilled in the art from consideration of the description set forth herein. It is intended that the specification, together with the examples, be considered exemplary only, with the scope and spirit of the invention being indicated by the claims which follow.

What is claimed is:

1. A method of hydraulic fracturing a subterranean formation which comprises introducing into the formation at a pressure sufficient to create or enlarge fractures in the formation a fracturing fluid having a pH from 8.5 to 11.0 comprising:
   (a) a hydratable polymer selected from the group consisting of underivatized guars and derivatized guars;
   (b) a crosslinking agent for crosslinking the hydratable polymer to form a polymer gel; and
   (c) an enzyme breaker comprising a mannanohydrolase enzyme that has an amino acid sequence that is at least 90% homologous to the amino acid sequence of SEQ ID NO:2.

2. The method of claim 1, wherein the downhole temperature of the subterranean formation is in excess of 180° F.

3. The method of claim 2, wherein the downhole temperature of the subterranean formation is in excess of 185° F.

4. The method of claim 1, wherein the mannanohydrolase enzyme has an amino acid sequence that is at least 95% homologous to the amino acid sequence of SEQ ID NO:2.

5. The method of claim 1, wherein the crosslinking agent contains boron or is capable of providing boron ions to the fluid.

6. The method of claim 1, wherein the hydratable polymer is underivatized guar.

7. A method of hydraulic fracturing a subterranean formation penetrated by a well comprising:
   (a) pumping into the well at a pressure sufficient to create or enlarge fractures in the formation a fracturing fluid having a pH from 8.5 to 11.0 comprising:
      (i) a hydratable polymer selected from the group consisting of underivatized guars and derivatized guars;
      (ii) a crosslinking agent for crosslinking the hydratable polymer to form a polymer gel;
      (iii) an enzyme breaker comprising a mannanohydrolase enzyme that has an amino acid sequence that is at least 90% homologous to the amino acid sequence of SEQ ID NO:2; and
      (iv) proppant; and
   (b) creating a partial monolayer of proppant in the created or enlarged fracture.

8. The method of claim 7, wherein the downhole temperature of the subterranean formation is in excess of 160° F.

9. The method of claim 7, wherein the hydratable polymer is underivatized guar.

10. The method of claim 7, wherein the mannanohydrolase enzyme has an amino acid sequence that is at least 95% homologous to the amino acid sequence of SEQ ID NO:2.

11. The method of claim 10, wherein the mannanohydrolase enzyme has an amino acid sequence that is at least 99% homologous to the amino acid sequence of SEQ ID NO:2.

12. A method of hydraulic fracturing a subterranean formation which comprises:
   (a) introducing into the formation at a pressure sufficient to create or enlarge fractures in the formation a fracturing fluid having a pH from 8.5 to 11.0 comprising:
      (i) a hydratable galactomannan gum;
      (ii) a crosslinking agent for crosslinking the galactomannan gum to form a polymer gel; and
      (iii) an enzyme breaker comprising a mannanohydrolase enzyme that has an amino acid sequence that is at least 90% homologous to the amino acid sequence of SEQ ID NO:2; and
   (b) reducing the viscosity of the fracturing fluid at a range of temperatures from 72° F. to at least 200° F.

13. The method of claim 12, wherein the fracturing fluid further comprises a pH regulating substance.

14. The method of claim 13, wherein the viscosity of the fracturing fluid is reduced by activating the enzyme breaker by the in-situ production of a Bronsted acid.

15. The method of claim 14, wherein the pH regulating substance is selected from the group consisting of organic anhydrides, acyl halides, sulfonyl halides, benzylic halides and a low molecular weight ester soluble in the fracturing fluid.

16. The method of claim 12, wherein the crosslinking agent is a borate or a boron releasing compound.

17. The method of claim 16, wherein the crosslinking agent is an organoborate, monoborate, polyborate, mineral borate, boric acid, sodium borate, a borate ore or a borate complexed organic compound.

18. The method of claim 12, wherein the enzyme breaker exhibits activity and has a temperature maximum in excess of 160° F.

19. The method of claim 18, wherein the enzyme breaker exhibits activity and has a temperature maximum in excess of 185° F.

20. The method of claim 19, wherein the enzyme breaker exhibits activity and has a temperature maximum in excess of 195° F.

\* \* \* \* \*

SEQUENCE LISTING

<160> NUMBER OF SEQ ID NOS: 2

<210> SEQ ID NO 1
<211> LENGTH: 1053
<212> TYPE: DNA
<213> ORGANISM: Artificial Sequence
<220> FEATURE:
<221> NAME/KEY: CDS
<222> LOCATION: (7)..(1044)
<223> OTHER INFORMATION: Caldocellum saccharolyticum

<400> SEQUENCE: 1

```
ggatcc atg cgc ctg aaa acc aaa atc cgc aaa aag tgg ctg tca gtg        48
       Met Arg Leu Lys Thr Lys Ile Arg Lys Lys Trp Leu Ser Val
        1               5                  10 ctg tgc act gta gtc ttt ctg ctg aat att ctg ttt att gcg aac gtt        96
Leu Cys Thr Val Val Phe Leu Leu Asn Ile Leu Phe Ile Ala Asn Val
15                  20                  25                  30 acc atc ctg cca aaa gta ggc gcg gct acc tcc aac gat ggt gtg gtt       144
Thr Ile Leu Pro Lys Val Gly Ala Ala Thr Ser Asn Asp Gly Val Val
                35                  40                  45 aaa att gat acc tcg acc ctg att ggt acc aat cat gct cat tgc tgg       192
Lys Ile Asp Thr Ser Thr Leu Ile Gly Thr Asn His Ala His Cys Trp
            50                  55                  60 tat cgc gat cgt ctg gat acc gcg ctg cgc gga att cgt agt tgg ggt       240
Tyr Arg Asp Arg Leu Asp Thr Ala Leu Arg Gly Ile Arg Ser Trp Gly
        65                  70                  75 atg aac tcg gta cgc gtc gtt ctg tct aat ggc tat cgc tgg aca aaa       288
Met Asn Ser Val Arg Val Val Leu Ser Asn Gly Tyr Arg Trp Thr Lys
    80                  85                  90 att ccg gcc agc gaa gtt gcc aac att att tcg ctg tcc cgc tcc ctg       336
Ile Pro Ala Ser Glu Val Ala Asn Ile Ile Ser Leu Ser Arg Ser Leu
95                  100                 105                 110 ggc ttc aaa gcc att att ctg gag gtg cat gat acc acc ggt tac ggt       384
Gly Phe Lys Ala Ile Ile Leu Glu Val His Asp Thr Thr Gly Tyr Gly
                115                 120                 125 gaa gat ggt gcg gcg tgc tcc ctg gca cag gca gtt gaa tat tgg aaa       432
Glu Asp Gly Ala Ala Cys Ser Leu Ala Gln Ala Val Glu Tyr Trp Lys
            130                 135                 140 gag atc aaa agc gtg ctg gat ggc aat gaa gat ttt gtc atc atc aat       480
Glu Ile Lys Ser Val Leu Asp Gly Asn Glu Asp Phe Val Ile Ile Asn
        145                 150                 155 att ggt aat gaa ccg tat ggt aat aac aac tat cag aac tgg gta aat       528
Ile Gly Asn Glu Pro Tyr Gly Asn Asn Asn Tyr Gln Asn Trp Val Asn
    160                 165                 170 gat act aag aat gca att aaa gcg ctg cgc gat gcc ggc ttt aag cat       576
Asp Thr Lys Asn Ala Ile Lys Ala Leu Arg Asp Ala Gly Phe Lys His
175                 180                 185                 190 acc atc atg gta gat gcg ccg aac tgg ggc cag gat tgg tcg aat acc       624
Thr Ile Met Val Asp Ala Pro Asn Trp Gly Gln Asp Trp Ser Asn Thr
                195                 200                 205 atg cgc gac aat gct cag tct att atg gaa gcc gat cca ctg cgt aat       672
Met Arg Asp Asn Ala Gln Ser Ile Met Glu Ala Asp Pro Leu Arg Asn
            210                 215                 220
```

| | | |
|---|---|---|
| ctg gta ttt agc att cac atg tac ggt gtc tat aat act gcg agc aaa<br>Leu Val Phe Ser Ile His Met Tyr Gly Val Tyr Asn Thr Ala Ser Lys<br>     225        230       235 | | 720 |
| gtg gaa gaa tat atc aaa agt ttt gtg gat aaa ggt ctg ccg ctg gtt<br>Val Glu Glu Tyr Ile Lys Ser Phe Val Asp Lys Gly Leu Pro Leu Val<br>240         245        250 | | 768 |
| atc ggc gaa ttc ggt cac cag cac act gat ggt gac cct gat gaa gag<br>Ile Gly Glu Phe Gly His Gln His Thr Asp Gly Asp Pro Asp Glu Glu<br>255         260       265       270 | | 816 |
| gcg atc gtt cgc tat gcc aaa cag tat aaa att ggc ctg ttt agt tgg<br>Ala Ile Val Arg Tyr Ala Lys Gln Tyr Lys Ile Gly Leu Phe Ser Trp<br>       275       280       285 | | 864 |
| agt tgg tgt ggg aac agc agt tac gtc ggt tac ctg gat atg gtg aat<br>Ser Trp Cys Gly Asn Ser Ser Tyr Val Gly Tyr Leu Asp Met Val Asn<br>         290       295       300 | | 912 |
| aac tgg gac ccg aac aac ccg acc cca tgg ggg cag tgg tat aaa aca<br>Asn Trp Asp Pro Asn Asn Pro Thr Pro Trp Gly Gln Trp Tyr Lys Thr<br>305         310       315 | | 960 |
| aat gcg atc ggc acg tca agc acg ccg acc ccg aca tcg act gtc acc<br>Asn Ala Ile Gly Thr Ser Ser Thr Pro Thr Pro Thr Ser Thr Val Thr<br>320         325       330 | | 1008 |
| cca acg cca ccg ccg cgc cag cac cag cat cgc caa taaaagctt<br>Pro Thr Pro Pro Pro Arg Gln His Gln His Arg Gln<br>335         340       345 | | 1053 |

<210> SEQ ID NO 2
<211> LENGTH: 346
<212> TYPE: PRT
<213> ORGANISM: Artificial Sequence
<220> FEATURE:
<223> OTHER INFORMATION: Calocellum saccharolyticum

<400> SEQUENCE: 2

Met Arg Leu Lys Thr Lys Ile Arg Lys Lys Trp Leu Ser Val Leu Cys
1       5         10         15

Thr Val Val Phe Leu Leu Asn Ile Leu Phe Ile Ala Asn Val Thr Ile
       20         25         30

Leu Pro Lys Val Gly Ala Ala Thr Ser Asn Asp Gly Val Val Lys Ile
     35         40         45

Asp Thr Ser Thr Leu Ile Gly Thr Asn His Ala His Cys Trp Tyr Arg
50         55         60

Asp Arg Leu Asp Thr Ala Leu Arg Gly Ile Arg Ser Trp Gly Met Asn
65         70         75         80

Ser Val Arg Val Val Leu Ser Asn Gly Tyr Arg Trp Thr Lys Ile Pro
         85         90         95

Ala Ser Glu Val Ala Asn Ile Ser Leu Ser Arg Ser Leu Gly Phe
        100        105       110

Lys Ala Ile Ile Leu Glu Val His Asp Thr Thr Gly Tyr Gly Glu Asp
     115         120         125

Gly Ala Ala Cys Ser Leu Ala Gln Ala Val Glu Tyr Trp Lys Glu Ile
130         135         140

Lys Ser Val Leu Asp Gly Asn Glu Asp Phe Val Ile Ile Asn Ile Gly
145         150         155         160

Asn Glu Pro Tyr Gly Asn Asn Asn Tyr Gln Asn Trp Val Asn Asp Thr
         165        170        175

Lys Asn Ala Ile Lys Ala Leu Arg Asp Ala Gly Phe Lys His Thr Ile
         180        185       190

Met Val Asp Ala Pro Asn Trp Gly Gln Asp Trp Ser Asn Thr Met Arg
     195         200         205

```
Asp Asn Ala Gln Ser Ile Met Glu Ala Asp Pro Leu Arg Asn Leu Val
    210             215             220
Phe Ser Ile His Met Tyr Gly Val Tyr Asn Thr Ala Ser Lys Val Glu
225             230             235             240
Glu Tyr Ile Lys Ser Phe Val Asp Lys Gly Leu Pro Leu Val Ile Gly
                245             250             255
Glu Phe Gly His Gln His Thr Asp Gly Asp Pro Asp Glu Glu Ala Ile
            260             265             270
Val Arg Tyr Ala Lys Gln Tyr Lys Ile Gly Leu Phe Ser Trp Ser Trp
        275             280             285
Cys Gly Asn Ser Ser Tyr Val Gly Tyr Leu Asp Met Val Asn Asn Trp
    290             295             300
Asp Pro Asn Asn Pro Thr Pro Trp Gly Gln Trp Tyr Lys Thr Asn Ala
305             310             315             320
Ile Gly Thr Ser Ser Thr Pro Thr Pro Thr Ser Thr Val Thr Pro Thr
            325             330             335
Pro Pro Pro Arg Gln His Gln His Arg Gln
            340             345
```